US009633577B2

(12) United States Patent
Constantine, III

(10) Patent No.: US 9,633,577 B2
(45) Date of Patent: Apr. 25, 2017

(54) CPR TRAINING SYSTEM AND METHODS

(71) Applicant: ZOLL MEDICAL CORPORATION, Chelmsford, MA (US)

(72) Inventor: Henry C. Constantine, III, Rochester, NY (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 0 days.

(21) Appl. No.: 13/633,391

(22) Filed: Oct. 2, 2012

(65) Prior Publication Data

US 2014/0093853 A1  Apr. 3, 2014

(51) Int. Cl.
  *G09B 23/28*  (2006.01)
  *A61B 5/02*  (2006.01)
  *A61B 5/0205*  (2006.01)
  *A61H 31/00*  (2006.01)

(52) U.S. Cl.
  CPC .............. *G09B 23/288* (2013.01); *A61B 5/02* (2013.01); *A61B 5/0205* (2013.01); *A61B 5/02055* (2013.01); *A61H 31/00* (2013.01)

(58) Field of Classification Search
  CPC . A61B 2562/0219; A61B 5/11; A61B 5/6892; A61B 5/7242; A61B 5/02; A61B 5/0205; A61B 5/02055; A61H 2201/5061; A61H 2201/5084; A61H 31/005; A61H 31/00; G09B 23/288
  USPC .................. 434/262, 265, 267; 600/300, 301
  See application file for complete search history.

(56) References Cited

U.S. PATENT DOCUMENTS

| 4,683,890 | A | 8/1987 | Hewson |
| 6,351,671 | B1 * | 2/2002 | Myklebust et al. ............... 607/5 |
| 6,356,785 | B1 | 3/2002 | Snyder et al. |
| 6,749,567 | B2 | 6/2004 | Davis et al. |
| 7,308,304 | B2 | 12/2007 | Hampton et al. |
| 2001/0047140 | A1 | 11/2001 | Freeman |
| 2004/0143298 | A1 | 7/2004 | Nova et al. |
| 2004/0210170 | A1 | 10/2004 | Palazzolo et al. |
| 2006/0015044 | A1 | 1/2006 | Stavland et al. |
| 2007/0010764 | A1 * | 1/2007 | Palazzolo et al. ............... 601/41 |
| 2007/0135739 | A1 * | 6/2007 | Halperin et al. ................ 601/41 |
| 2007/0197926 | A1 | 8/2007 | Danehorn et al. |
| 2007/0299473 | A1 | 12/2007 | Matos |

(Continued)

FOREIGN PATENT DOCUMENTS

| DE | 3110915 A1 | 12/1982 |
| WO | 2006006871 A2 | 1/2006 |

OTHER PUBLICATIONS

Aramendi et al. "A Simple Effective Filtering Method for Removing CPR Caused Artefacts from Surface ECG Signals". Computers in Cardiology. Sep. 25, 2005.

(Continued)

*Primary Examiner* — Eddy Saint-Vil
(74) *Attorney, Agent, or Firm* — ZOLL Medical Corporation

(57) ABSTRACT

A system including a chest compression sensor configured to detect at least one parameter corresponding to chest compressions of a subject and an electrocardiogram signal simulator configured to generate a simulated electrocardiogram signal and combine and/or modify the simulated electrocardiogram signal with an output of the chest compression sensor to produce a simulated electrocardiogram signal with a CPR artifact.

31 Claims, 8 Drawing Sheets

(56) References Cited

U.S. PATENT DOCUMENTS

| | | |
|---|---|---|
| 2008/0208082 A1* | 8/2008 | Nysaether et al. ........... 600/595 |
| 2010/0164612 A1 | 7/2010 | Koyrakh |
| 2010/0292748 A9 | 11/2010 | Stickney et al. |
| 2011/0034836 A1 | 2/2011 | Halperin et al. |
| 2011/0066054 A1 | 3/2011 | Yazicioglu et al. |
| 2011/0105930 A1 | 5/2011 | Thiagarajan et al. |
| 2012/0150169 A1 | 6/2012 | Zielinksi et al. |
| 2012/0191024 A1* | 7/2012 | Halperin et al. ................ 601/41 |
| 2013/0184600 A1 | 7/2013 | Tan et al. |

OTHER PUBLICATIONS

Romero et al. "Motion Artifact Reduction in Ambulatory ECG Monitoring: An Integrated System Approach". Wireless Health. Oct. 10, 2011.

\* cited by examiner

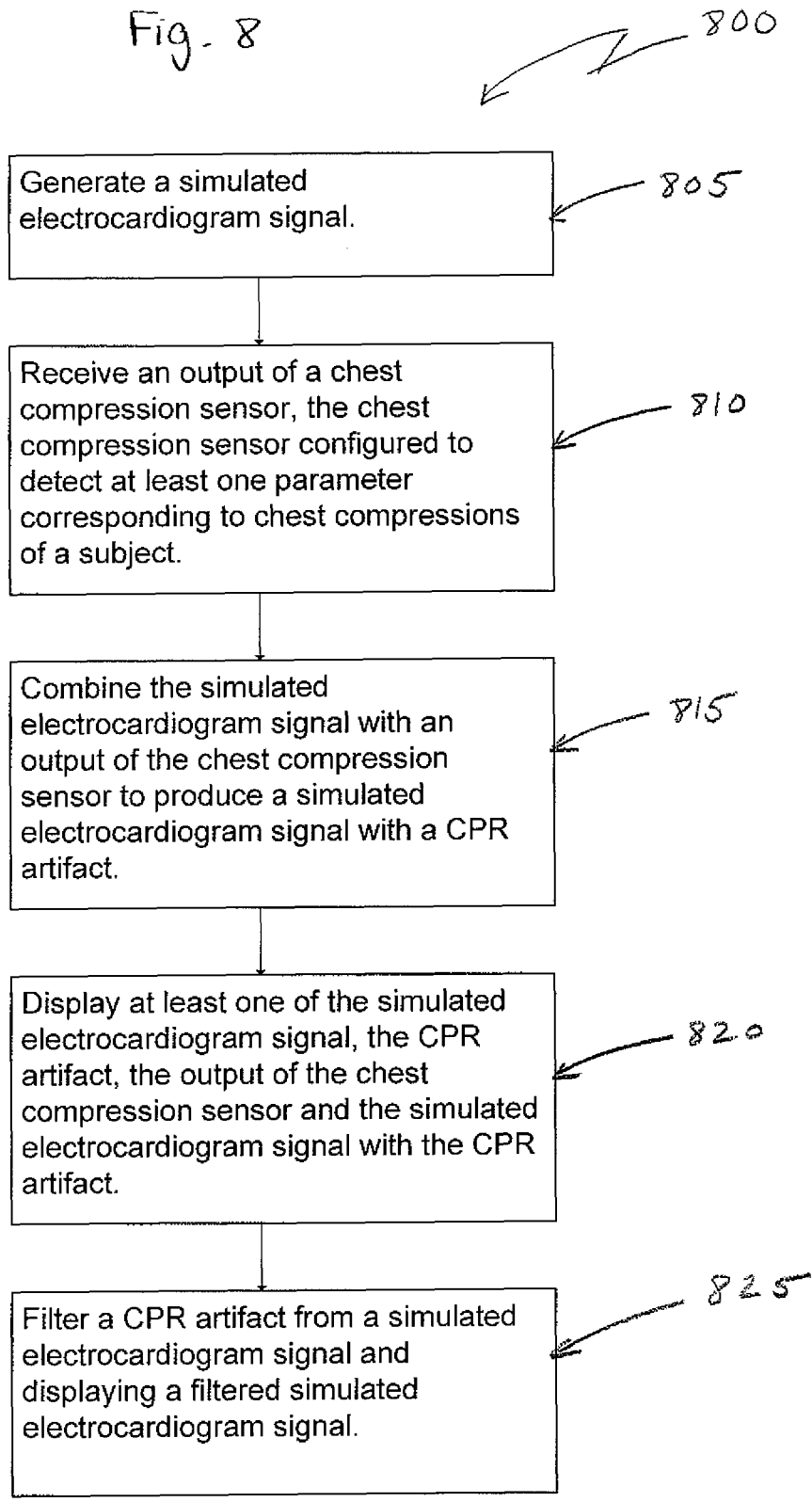

CPR TRAINING SYSTEM AND METHODS

TECHNICAL FIELD

The invention relates generally to methods and associated equipment for training users of medical devices.

BACKGROUND

Automated External Defibrillators (AEDs) have been shown to be very effective in saving lives, when used quickly and properly. Depending on the condition of the subject, an effective treatment often combines the delivery of appropriately timed defibrillation therapy with continuous cardio-pulmonary resuscitation (CPR).

Advanced AED devices have been developed that can accommodate this simultaneous emergency treatment protocol. A key to expanding this life saving procedure has been the development of AED devices that can be used by non-medical personnel with limited training.

SUMMARY

Various aspects of examples of the invention are set out in the claims. A system comprises a chest compression sensor configured to detect at least one parameter corresponding to chest compressions of a subject and an electrocardiogram signal simulator configured to generate a simulated electrocardiogram signal and combine the simulated electrocardiogram signal with an output of the chest compression sensor to produce a simulated electrocardiogram signal with a CPR artifact.

According to a second aspect of the present invention, a method comprises generating a simulated electrocardiogram signal and receiving an output of a chest compression sensor. The chest compression sensor is configured to detect at least one parameter corresponding to chest compressions of a subject. The method further comprises combining the simulated electrocardiogram signal with an output of the chest compression sensor to produce a simulated electrocardiogram signal with a CPR artifact and displaying at least one of the simulated electrocardiogram signal, the CPR artifact, the output of the chest compression sensor and the simulated electrocardiogram signal with the CPR artifact.

According to a third aspect of the present invention, a system comprises at least one processor and at least one memory including computer program code. The at least one memory and the computer program code is configured with the at least one processor to cause the system to generate a simulated electrocardiogram signal and receive an output of a chest compression sensor. The chest compression sensor is configured to detect at least one parameter corresponding to chest compressions of a subject. The system is further configured to combine the simulated electrocardiogram signal with an output of the chest compression sensor to produce a simulated electrocardiogram signal with a CPR artifact and display at least one of the simulated electrocardiogram signal, CPR artifact, output of the chest compression sensor and simulated electrocardiogram signal with the CPR artifact.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 8 is a flow diagram depicting a method according to an example embodiment of the invention.

DETAILED DESCRIPTION

Figure 1:
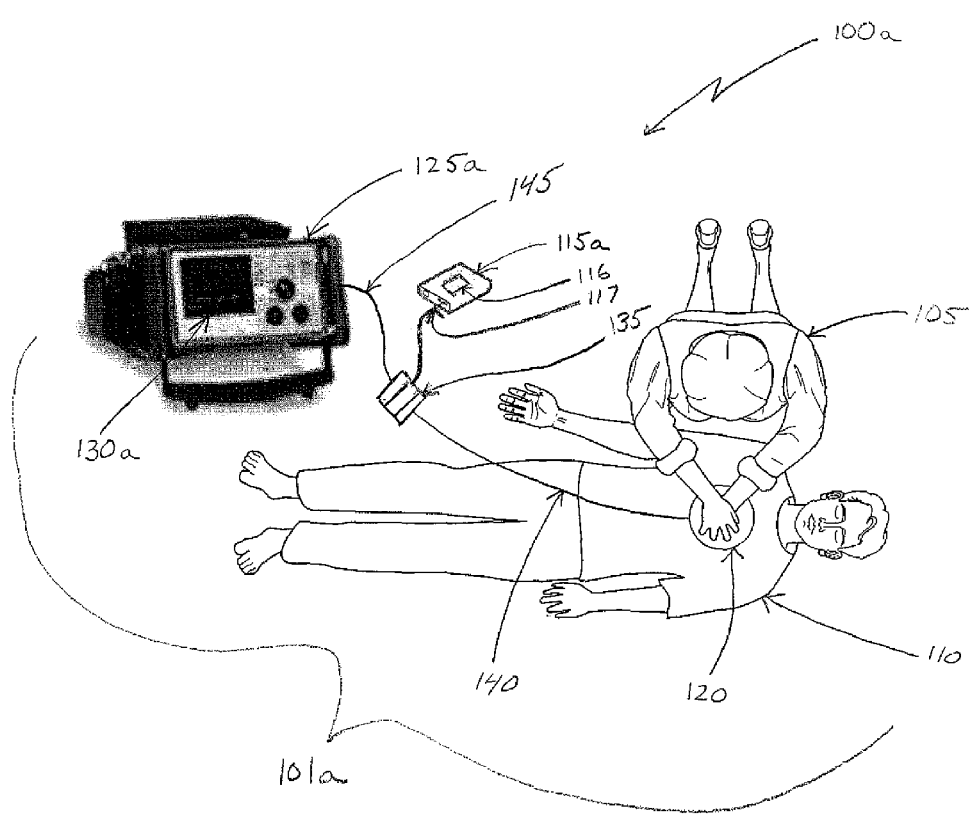
FIG. 1 is a diagram showing a simulated emergency response scene and a CPR training system including a device and external ECG signal simulator according to an example embodiment of the invention.

FIG. 1 is a diagram showing a simulated emergency response scene 100a and a CPR training system 101a including a device 125a and external ECG signal simulator 115a according to an example embodiment of the invention. In the embodiment, a CPR training system comprises an ECG signal simulator such as ECG signal simulator 115a that communicates with a chest compression sensor such as chest compression sensor 120. ECG signal simulator 115a modifies a simulated ECG output signal in real time based on the actual chest compressions being performed by trainee 105 on subject 110. In an embodiment, ECG signal simulator 115a combines an internally generated ECG signal with an output of the chest compression sensor to produce an ECG signal with a CPR artifact in real time.

In an embodiment, ECG signal simulator 115a is configurable by a user to provide various simulated ECG waveforms such as but not limited to ventricular fibrillation (fine and course), ventricular tachycardia, atrial fibrillation, atrial ventricular block (third degree), absolute arrhythmia, pulseless electrical activity, asystole, and normal sinus rhythm. For training purposes, ECG signal simulator 115a may be further configurable to provide various sequential combinations of simulated ECG waveforms such as but not limited to ventricular fibrillation and then normal sinus rhythm, ventricular tachycardia and then asystole, and so on. ECG signal simulator 115a may be configurable to provide any number or combination of sequential ECG waveforms useful for providing instruction to a trainee.

Further, ECG signal simulator 115a may include a user interface such as user interface 116 to enable a user to select particular waveforms or combinations of waveforms. In an embodiment, ECG signal simulator 115a comprises a touch screen display 116, however, ECG signal simulator 115a may comprise any number of input and/or output elements as part of the user interface such as but not limited to buttons, knobs, switches and/or the like.

In an embodiment, ECG signal simulator 115a comprises at least one communication interface, such as communication interface 117. A communication interface is a wired or wireless interface, which is capable of transmitting and/or receiving signals. In the embodiment, the communication interface is capable of receiving signals from CPR sensor 120. The communication interface is capable of transmitting signals related to at least one of an ECG simulated signal and CPR artifact signal. Signals from ECG simulator 115a may be transmitted through interface 135 to a display, medical monitoring device, AED or other device capable of displaying data related to the signals such as device 125a.

An ECG signal simulator may be disposed as a standalone unit such as ECG signal simulator 115a. However, the ECG simulator need not be a physically separate device that is required to be plugged into device 125a. As further described in FIG. 4, the ECG signal simulator may be disposed within a medical monitoring device such as device 125b of FIG. 4. In another embodiment, ECG signal simulator may be disposed in a mannequin such as mannequin 110. The mannequin can be instrumented with an ECG signal simulator so that the ECG signal may be read directly by an applied electrode system.

Figure 2:
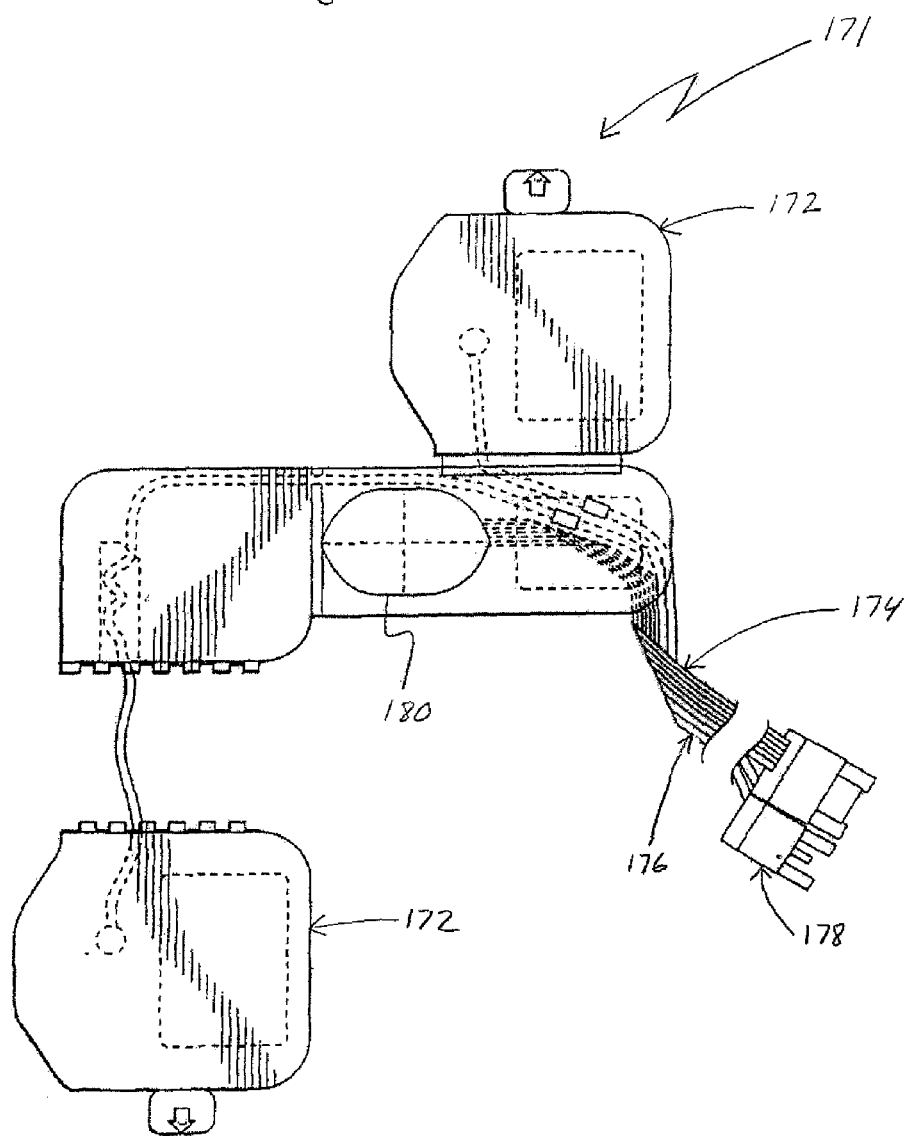
FIG. 2 is a diagram showing a chest compression sensor system according to an embodiment of the invention.

The chest compression sensor 120 may be any chest compression sensor system, such as a CPR-D•padz® accelerometer-based sensor system available from Zoll Medical Corporation as shown in FIG. 2 and described more fully below. Signals from a CPR sensor may comprise data from at least one accelerometer, which may be disposed within the CPR sensor. Accelerometer data may include but are not limited to data related to least one of acceleration, velocity, displacement, amplitude, rate of CPR compressions and the like.

A device 125a comprising display 130a may be used to display at least one of the ECG simulated signal, the CPR artifact signal and the ECG signal complicated by the CPR artifact. Device 125a may be any device comprising a display, which is capable of displaying ECG waveforms. For example, device 125a may be any type of AED, medical monitoring device, display and/or the like such as but not limited to an AED E-Series Monitor Defibrillator manufactured by the Zoll Medical Corporation of Chelmsford, Mass.

According to FIG. 1, trainee 105 performs chest compressions on a mannequin 110 in an effort to improve her knowledge and performance in the delivery of CPR. A trainee may be a lay person with little or no experience in CPR, emergency medical technician (EMT), a police officer, firefighter, or a medical professional such as a physician or nurse, and/or the like. Further, trainee 105 may receive instruction and feedback with respect to her performance of CPR and on how to use certain medical devices, such as ECG signal simulator 115a and device 125a. The instructions and/or trainee feedback may be provided by device 125a, for example, when display device 125a is an AED such as an AED Plus manufactured by the Zoll Medical Corporation. In this way, the device can be used for training a rescuer in a simulated emergency situation with accommodation for ECG signal input complicated by an actual CPR artifact.

When device 125a is a medical monitoring device such as an AED, device 125a can react in a similar manner as it would in the event of a real-life emergency on a subject, including providing a defibrillation therapy shock when conditions warrant. A trainee such as trainee 105 can learn how the medical monitoring device responds to a subject's condition and how the trainee's actions during CPR affect the course of events. By replicating a real-life emergency, the trainee is placed in the best position to react quickly and effectively in the event of an actual real-life emergency.

In an embodiment, when ECG signal simulator 115a generates a simulated true ECG signal (ventricular fibrillation (fine and course), ventricular tachycardia, atrial fibrillation, atrial ventricular block (third degree), absolute arrhythmia, pulseless electrical activity, asystole, and normal sinus rhythm, etc.), device 125a prompts the trainee 105 to begin CPR. As chest compressions are initiated by trainee 105 and sensed by the CPR sensor, the output of the CPR sensor is input to each of device 125a and the ECG signal generator 115a. Device 125a monitors both the rate and the magnitude of compressions and directs the trainee accordingly. For example, if device is an AED manufactured by Zoll Medical Corporation, Zoll's Real CPR Help® functionality guides the trainee to ensure optimal CPR protocol, in accordance with AHA guidelines. Device 125a monitors compression data from the CPR sensor in real time and provides an adaptive metronome to help the trainee with the proper rate and depth, saying "Push harder" or "Good compressions," as needed. CPR compression rate and/or depth can also be displayed on display 130a. In this manner, the trainee rapidly achieves and maintains the correct rate and depth of chest compressions during CPR.

If the trainee 105 pauses CPR, since device 125a is directly connected to the CPR sensor, the device 125a may recognize that CPR is not being performed and directs the trainee to "Start CPR." The onset of CPR compressions may cause the output of the ECG signal simulator to change in real time, consistent with the rate and depth of CPR compressions being performed.

Device 125a may monitor the changing ECG signal complicated by chest compressions and, consistent with the teachings of U.S. Pat. No. 6,865,413 ("'413 patent"), which is incorporated herein by reference in its entirety, applies a correction to the changing ECG signal to separate the CPR-induced artifact in the signal from the underlying simulated true ECG signal.

When the device 125a determines that the subject's condition is appropriate for defibrillation therapy, device 125a may direct the trainee to stop CPR and deliver a shock to the mannequin. To avoid actual delivery of the shock to the electrodes attached to the mannequin, the connector plug intercept may include a suitably sized resistor, to dissipate safely the electromagnetic energy, or shunt the shock energy to the simulator where it is dissipated.

In this manner, a fully operational, field usable device 125a can be employed in a training setting with a mannequin to replicate as realistically as possible the operation and functioning of an advanced AED system. Neither the AED device nor the trainee is deceived as to the effect of the CPR compression data on the ECG signal. The generated baseline simulated true ECG signal is modified in real time to include a CPR compression artifact consistent with the CPR compressions being performed by the trainee. Device 125a, with the benefit of its integrated internal CPR artifact functionality, effectively subtracts out the CPR artifact from its received signal, to monitor the underlying true ECG signal.

Device 125a in accordance with embodiments of the invention accurately presents to a trainee, in a convincing fashion, the effects of CPR compressions being performed by the trainee. Various signals, including the CPR sensor output (e.g., acceleration, velocity, and displacement), the CPR artifact, and the ECG signal with and without the CPR artifact can be displayed individually or in various combinations to the trainee, to provide additional understanding of the electrophysiological effects of CPR on the victim and operation of the AED device. A trainer selectable mode switch may be provided on the ECG generator for this purpose. Accordingly, the trainee can appreciate that the AED device is able to analyze the underlying heart rhythm, despite the CPR artifact.

Device 125*a* can be configured by user for "training mode" to permit training and demonstration functionality, as well as emergency treatment capability, in a single device. Alternatively, control software or hardware in device 125*a* could be adapted to recognize the insertion of the connector plug intercept and not deliver a high energy shock to the electrodes, but otherwise perform in a real life manner to simulate a real rescue. Further, the device 125*a* may be used in a "normal operating mode" which effectively turns off the ECG simulation capability for normal operation.

Device 125*a* may be configured with a mode switch, that can be selected by the trainer or the trainee to display the CPR artifact laden ECG signal or the underlying ECG signal with the CPR artifact filtered out. The CPR artifact laden ECG signal depicts an artifact synchronized with the actions of the rescuer on the subject, correlated to CPR sensor compression depth and rate.

FIG. 2 is a diagram showing a chest compression sensor system 171 according to an embodiment of the invention. A chest compression sensor system 171 may be any chest compression sensor, such as a CPR-D•padz® accelerometer-based sensor system available from Zoll Medical Corporation. In an embodiment, chest compressor sensor 120 of FIG. 1 is chest compression sensor system 171.

The CPR-D•padz® system comprises a pair of ECG signal pickup electrodes 172 configured to attach adhesively to a subject's chest to acquire data indicative of the subject's heart rhythm and to convey a defibrillating shock, if appropriate. The electrode pair 172 is integrated with a chest compression sensor pad 180 in a one-piece, pre-connected apparatus. For example, see U.S. Pat. No. 7,245,974, the disclosure of which is incorporated herein by reference in its entirety. Conventional AED systems require that the rescuer use and place two separate electrodes. By using CPR hand placement as a landmark, the combined system can be positioned and adhered to the mannequin's chest quickly and in the appropriate location and orientation.

The chest compression sensor system 171 further comprises a communication interface 178 comprising sensor wires 174 and electrode wires 176. In an embodiment, the communication interface 178 couples with a device such as device 125*a* of FIG. 1. In another embodiment, the communication interface 178 couples with an intercept plug such as intercept plug 135 of FIG. 1 and/or intercept plug 165 of FIG. 3. In an embodiment, the communication interface couples with a ECG signal simulator such as ECG signal simulator 115*a*.

Figure 3:
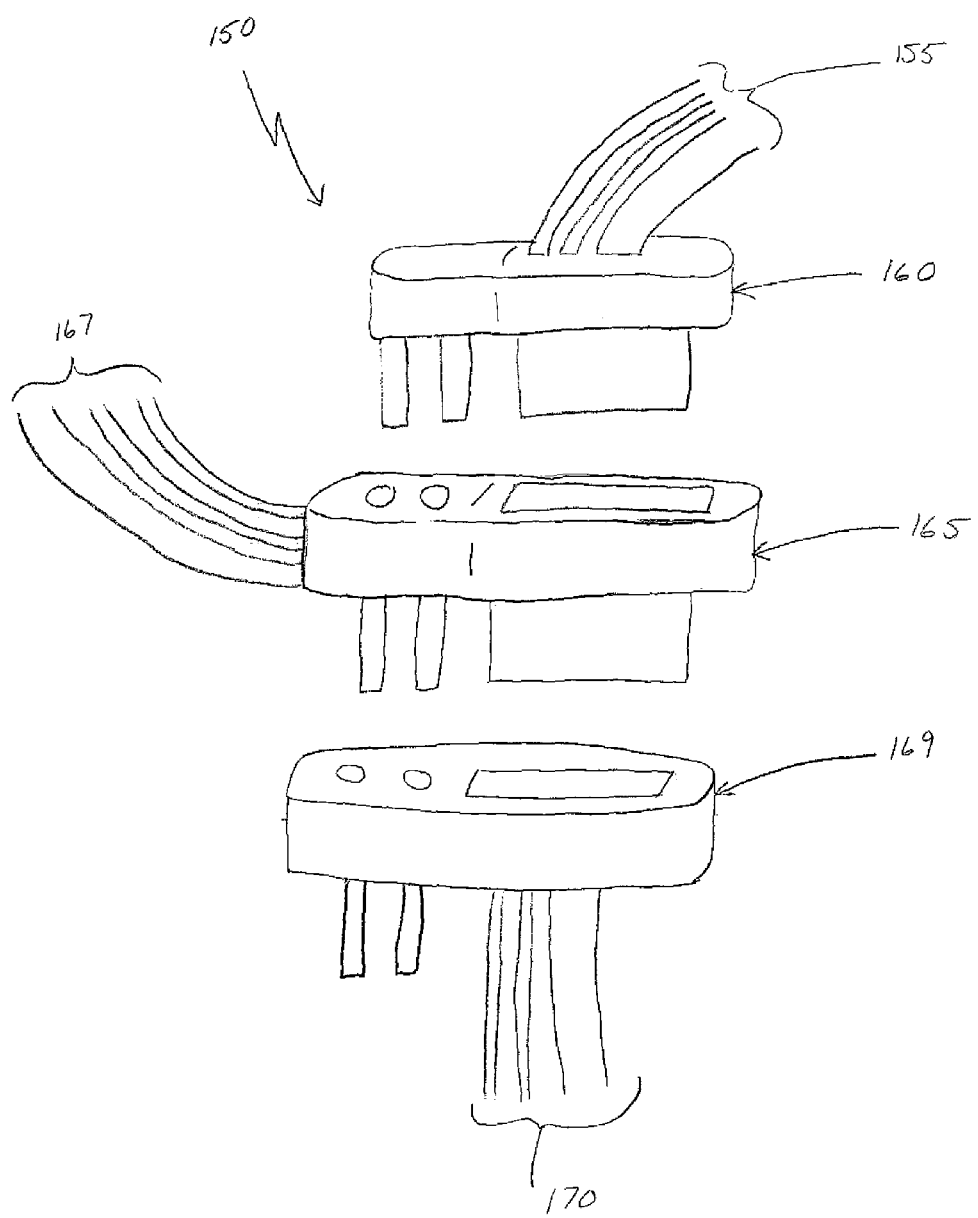
FIG. 3 is an exploded view of an assembly comprising a sensor/electrode connector of a chest compression sensor, a connector plug intercept of an ECG signal simulator, and a device connector according to an example embodiment of the invention.

FIG. 3 is an exploded view of an assembly 150 comprising a sensor/electrode connector 160 of a chest compression sensor, a connector plug intercept 165 of an ECG signal simulator, and a device connector 169 according to an example embodiment of the invention. Assembly 150 is configured to carry signals from a chest compression sensor such as chest compression sensor system 171 of FIG. 2 through sensor/electrode connector 160 and connection plug intercept 165 to at least one of an ECG signal simulator and a device such as device 125*a* of FIG. 1. In an embodiment, leads 155 are configured to electrically couple assembly 150 with a chest compression sensor such as chest compression sensor system 171 of FIG. 2.

Assembly 150 is further configured to carry at least one of a simulated ECG signal, chest compression artifact signal, and a modified simulated ECG signal from an ECG signal simulator such as ECG signal simulator 115*a* of FIG. 1 to a device such as device 125*a* of FIG. 1. In an embodiment, leads 167 are configured to electrically couple assembly 150 with an ECG signal simulator such as ECG signal simulator 115*a*. In an embodiment, leads 170 are configured to electrically couple assembly 150 with a device such as device 125*a*. In an embodiment, assembly 150 is interface 135 of FIG. 1.

In an embodiment, assembly 150 may further couple defibrillator electrodes such as electrodes 172 of FIG. 2 with a device such as an AED. In an embodiment, to avoid actual delivery of a shock from an AED to the electrodes, which may be attached to a mannequin, connector plug intercept 165 can include a suitably sized resistor, to safely dissipate the electric shock energy or shunt the shock energy to the ECG signal simulator where it is dissipated. The ECG simulator optionally can include circuitry for delivering a simulated subject impedance signal to the AED device. In another embodiment, the ECG signal simulator can include circuitry for shunting a defibrillation therapy output signal of an AED device.

Figure 4:
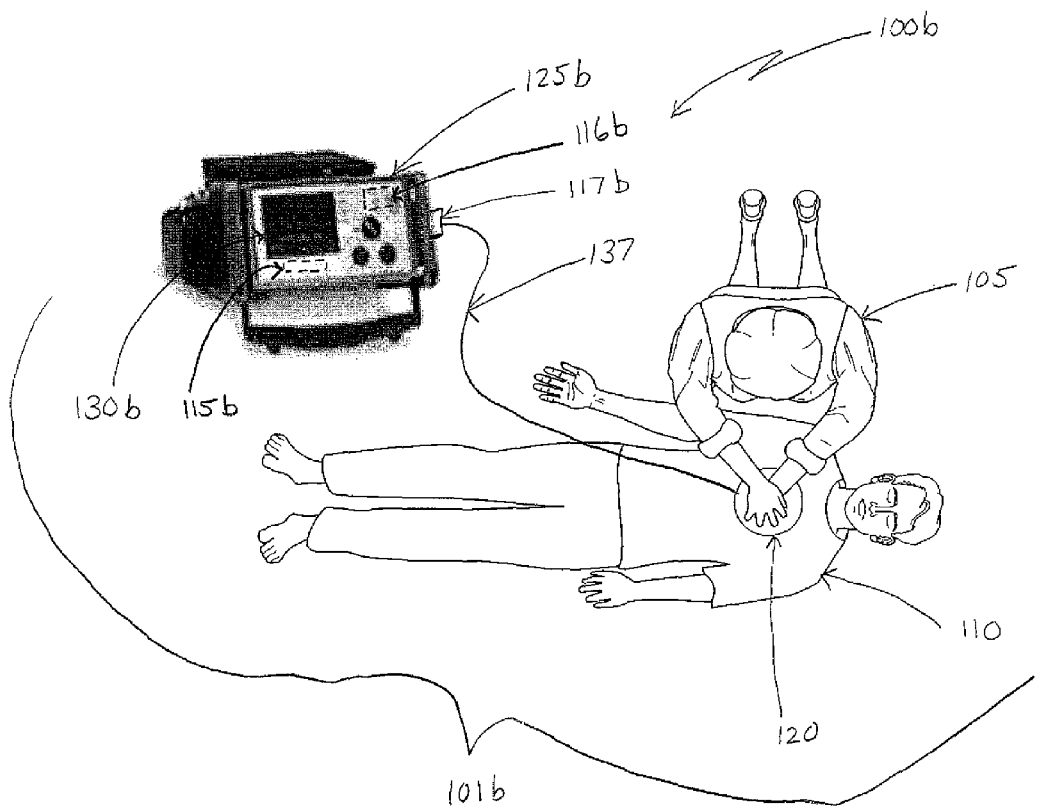
FIG. 4 is a diagram showing a simulated emergency response scene and a CPR training system including a device and an internal ECG signal simulator according to an example embodiment of the invention.

FIG. 4 is a diagram showing a simulated emergency response scene 100*b* and a CPR training system 101*b* including a device 125*b* and an internal ECG signal simulator 115*b* according to an example embodiment of the invention. In an embodiment, a CPR training system such as CPR training system 101*b* comprises an ECG signal simulator 115*b* disposed within a device such as device 125*b* and a chest compression sensor such as chest compression sensor 120. ECG signal simulator 115*b* modifies a simulated ECG output signal based on actual chest compressions being performed by a trainee such as trainee 105. In an embodiment, ECG signal simulator 115*b* is an internal version of external ECG signal simulator 115*a* of FIG. 1 and comprises substantially the same functionality as ECG signal simulator 115*a* of FIG. 1. Device 125*b* may be used to display at least one of the ECG simulated signal, the CPR artifact signal and the ECG signal complicated by the CPR artifact signal. In this way, the display device can be used for training a rescuer in a simulated emergency situation with accommodation for ECG signal input complicated by an actual CPR artifact.

The chest compression sensor 120 may be any chest compression sensor system, such as a CPR-D•padz® accelerometer-based sensor system available from Zoll Medical Corporation as shown in FIG. 2 and described more fully below.

A device such as device 125*b* may be any device capable of displaying an ECG waveform, which includes embedded ECG signal simulator 115*b*. For example, device 125*b* may be any type of AED, medical monitoring device, display and/or the like such as but not limited to an AED E-Series Defibrillator manufactured by the Zoll Medical Corporation of Chelmsford, Mass.

When device 125*b* is an AED used with CPR training system 101*b* according to an embodiment, the AED can react in a similar manner as it would in the event of a real-life emergency on a subject, including providing a defibrillation therapy shock when conditions warrant. A trainee such as trainee 105 can learn how the AED responds to a subject's condition and how the trainee's actions during CPR affect the course of events as described above for trainee 105 of FIG. 1.

In FIG. 4, trainee 105 performs chest compressions on a mannequin 110 in an effort to improve her knowledge and performance in the delivery of CPR. Further, trainee 105 may receive instruction and feedback with respect to her performance of CPR and/or on how to use certain medical devices, for example, medical monitors and defibrillators, ECG signal simulator 115b and display device 125. In an embodiment, the instructions and/or feedback may be provided by display device 125b, for example, when display device 125b is an AED such as an AED Plus manufactured by the Zoll Medical Corporation of Chelmsford, Mass.

In an embodiment, ECG signal simulator 115b is configurable to provide various simulated ECG waveforms such as but not limited to ventricular fibrillation (fine and course), ventricular tachycardia, atrial fibrillation, atrial ventricular block (third degree), absolute arrhythmia, pulseless electrical activity, asystole, and normal sinus rhythm. For training purposes, ECG signal simulator 115b may be configurable to provide various sequential combinations of simulated ECG waveforms such as but not limited to ventricular fibrillation and then normal sinus rhythm, ventricular tachycardia and then asystole, and so on. ECG signal simulator 115b may be configurable to provide any number or combination of sequential ECG waveforms useful for providing instruction to a trainee.

Further, ECG signal simulator 115b may include a user interface such as user interface 116b to enable a user to select particular waveforms or combinations of waveforms. In an embodiment, ECG signal simulator 115b comprises a touch screen display 116b, however, ECG signal simulator 115b may comprise any number of input and/or output elements as part of a user interface such as but not limited to buttons, knobs, switches and/or the like.

In an embodiment, ECG signal simulator 115b comprises at least one communication interface, such as communication interface 117b. A communication interface is a wired or wireless interface, which is capable of transmitting and/or receiving signals. In the embodiment, the communication interface is capable of receiving signals from a chest compression sensor, such as chest compression sensor 120. Signals from a chest compression sensor may comprise CPR artifact data from at least one accelerometer, which may be disposed within the chest compression sensor. Accelerometer data may include but is not limited to data related to least one of acceleration, velocity, displacement, amplitude, rate of CPR compressions and the like. In the embodiment, the communication interface is capable of transmitting signals related to at least one of an ECG simulated signal and CPR artifact signal.

Figure 5:
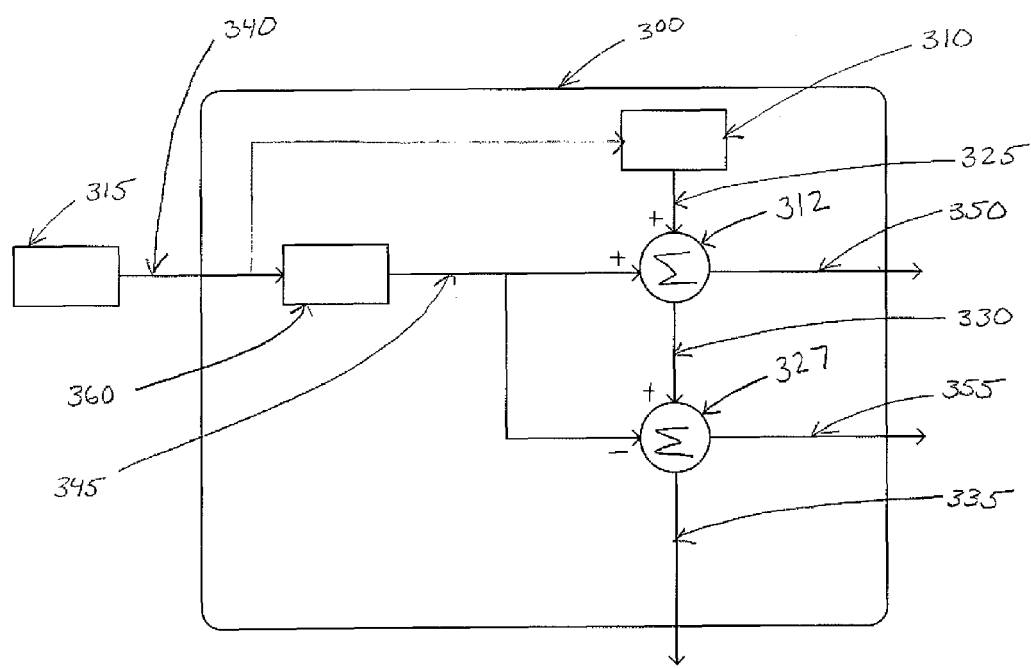
FIG. 5 is a diagram of an ECG signal simulator and a chest compression sensor according to an example embodiment of the invention.

FIG. 5 is a diagram of an ECG signal simulator 300 and a chest compression sensor 315 according to an example embodiment of the invention. In an embodiment, ECG signal simulator 300 is ECG signal simulator 115a of FIG. 1. In another embodiment, ECG signal simulator 300 is ECG signal simulator 115b of FIG. 4.

Figure 6:
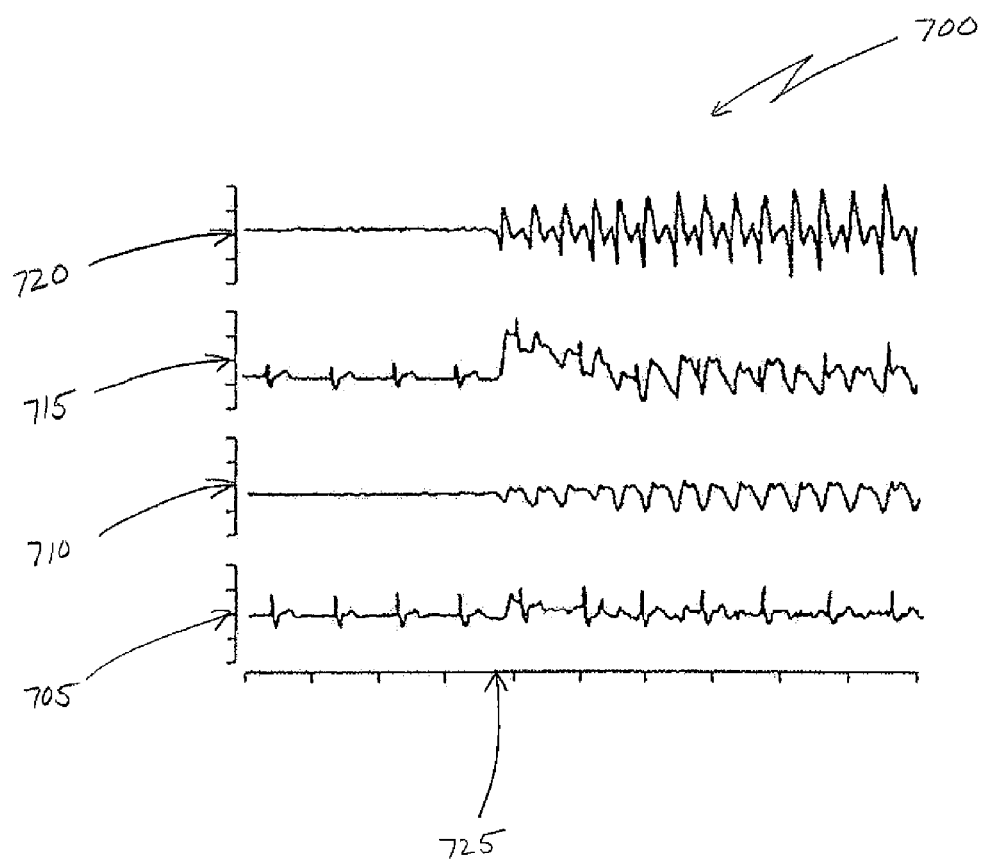
FIG. 6 is a schematic representation of various time-dependent, related waveforms associated with CPR.

In an embodiment, ECG signal simulator 300 comprises a signal generator 310, which is configured to produce a simulated true ECG signal such as but not limited to ventricular fibrillation (fine and course), ventricular tachycardia, atrial fibrillation, atrial ventricular block (third degree), absolute arrhythmia, pulseless electrical activity, asystole, and normal sinus rhythm. In an embodiment, ECG signal generator is configurable by a user to provide any one simulated ECG signal or various configurable sequential combinations of simulated ECG waveforms such as but not limited to ventricular fibrillation and then normal sinus rhythm, ventricular tachycardia and then asystole, and so on. For example, waveform 705 of FIG. 6 may represent output 325 of ECG signal simulator.

A chest compression sensor 315, which may utilize at least one accelerometer, provides chest compression data to the ECG signal simulator as input signal 340. In the embodiment, when a user provides chest compressions using chest compression sensor 315 to a subject, the sensor produces chest compression signal 340. An example waveform depicting a chest compression signal 340 is shown as signal 710 of FIG. 6, wherein reference 725 represents a time when CPR begins. An example waveform depicting an actual accelerometer signal is shown as signal 720 of FIG. 6. Chest compression sensor data may include but is not limited to data related to least one of acceleration, velocity, displacement, amplitude, rate of CPR compressions and the like. A chest compression sensor may be any type of chest compression sensor such as but not limited to chest compression sensor 171 of FIG. 2, chest compression sensor 120 of FIGS. 1 and 4.

In an embodiment, input signal 340 feeds ECG signal generator 310 and transfer function 360. When ECG signal generator 310 is configured to produce a ventricular fibrillation waveform, ECG signal generator 310 may modify received input signal 340 to provide a ventricular fibrillation waveform with a higher amplitude and/or frequency relative to the amplitude and/or frequency of the corresponding chest compressions detected by chest compression sensor 315. Simultaneously, the simulated ECG signal 325 is modified by signal modifier 312 to include a CPR artifact signal 345 correlated with the actual rate and depth of compressions being performed. The signal modification can be performed in accordance with the teaching of the '413 patent or similar technique. In an embodiment, the influence of the CPR compressions can be modeled as the output of a linear system perturbed by the actual chest compression sensor signal. For example, output 345 of transfer function 360 can be summed with the simulated true ECG signal 325 to produce a simulated ECG signal with true CPR artifact 350, which tracks the influence of the actual CPR compressions being performed. For example, a simulated true ECG signal with true CPR artifact is depicted as waveform 715 of FIG. 6. When CPR is not being performed, the CPR sensor input 345 to the summing junction 312 is zero and signals 350 and 330 represent an unmodified simulated ECG signal. The onset of chest compressions causes the output of the ECG signal generator to change in real time, consistent with the rate and depth of CPR compressions being performed.

In an embodiment, a signal modifier 327 may receive as inputs simulated ECG signal with true CPR artifact 330 and chest compression signal 345. Signal modifier 327 may be configured to produce signal 335, which represents the simulated ECG signal with a removed or substantially reduced CPR artifact component signal. For demonstration purposes, in this way, a trainee such as trainee 105 of FIG. 4 may observe CPR artifact reduction technology in a simulated environment.

Figure 7:
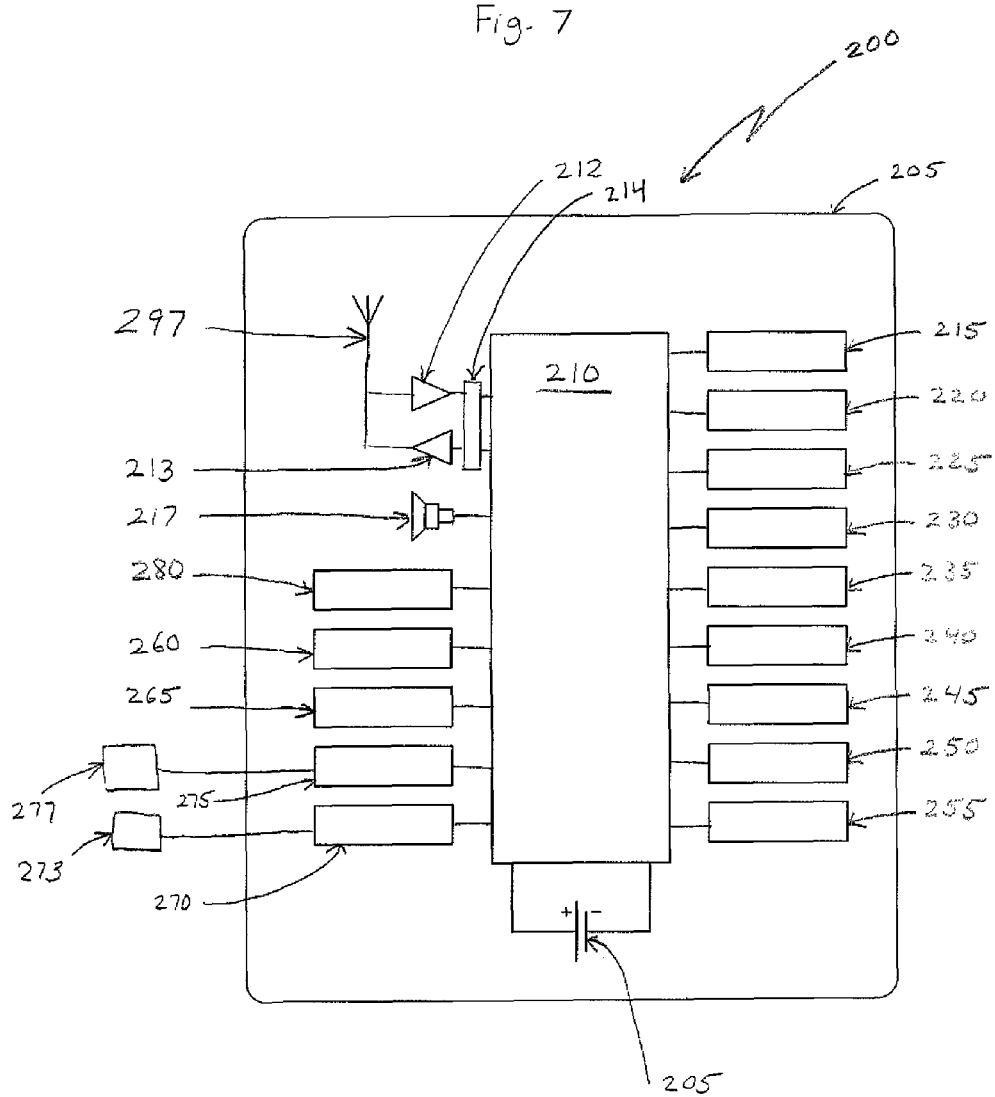
FIG. 7 is a block diagram of a system comprising a chest compression sensor and an ECG signal simulator, the ECG signal simulator disposed within a medical monitoring device according to an example embodiment of the invention.

FIG. 7 is a block diagram of a system 200 comprising a chest compression sensor 273 and an ECG signal simulator 255, the ECG signal simulator 255 disposed within a medical monitoring device such as medical monitoring device 205 according to an example embodiment of the invention. In an embodiment, a medical monitoring device 205 is a defibrillator such as but not limited to the Zoll X-Series Monitor Defibrillator manufactured by Zoll Medical Corporation of Chelmsford, Mass. In an embodiment, ECG signal simulator 255 is ECG signal simulator 300 of FIG. 5. In an embodiment, chest compression sensor 273 is chest compression sensor 315 of FIG. 5. In an embodiment, chest compression sensor 273 is chest compression sensor 120 of FIG. 4.

Medical monitoring device 205 further comprises at least one memory such as volatile memory 225 and/or a non-volatile memory 230. Volatile memory 225 may comprise a cache area for the temporary storage of data. Medical monitoring device 205 may further comprise non-volatile memory 230, which may be embedded and/or removable. The non-volatile memory 230 may further comprise an electrically erasable programmable read only memory (EE-PROM), flash memory, and/or the like. In an embodiment, medical monitoring device 205 may use memory to store any number of pieces of information and/or data to implement one or more features of medical monitoring device 205 such as the defibrillation unit 235 or ECG signal simulator 255.

Medical monitoring device 205 may comprise at least one processor such as processor 210 and may comprise at least one other processing component. Processor 210 may comprise circuitry for implementing medical monitoring features such as but not limited to ECG signal simulation, signal modification, defibrillation as well as other medical monitor functionality. For example, the at least one processor 210 may comprise a digital signal processor device, a microprocessor device, a digital to analog converter, other support circuits, and/or the like. Further, the processor 210 may comprise features to operate one or more software programs. In an embodiment, the processor 210 may be capable of operating a software program to implement functionality of the ECG signal simulator, defibrillator signal modification, signal filtering, defibrillation, connectivity as well as other medical monitor functionality. Further, the connectivity program may allow the medical monitoring device 205 to transmit and receive Internet and/or cellular data, such as but not limited to voice, text, email messages, location-based content, web page content, fax content and/or the like. Further, in an embodiment, processor 220 is configured to execute a software program for configuring and/or operating the ECG signal simulator 255. In an embodiment, processor 220 is configured to of execute a software program for configuring chest compression sensor 273.

In an embodiment, the medical monitoring device 205 comprises at least one antenna 297 to communicate with a transmitter 213 and a receiver 212. Transmitter 213 and/or receiver 212 are coupled with a network interface 214 for transmitting and receiving data with devices such as other medical equipment or emergency medical services centers. Processor 210 provides at least one signal to the transmitter 213 and receives at least one signal from receiver 212. Further, transmitter 213 and/or receiver 212 coupled with network interface 214 may be configured to transmit and receive voice communications such as with emergency medical personnel.

Further, the medical monitoring device 205 may further comprise an identifier, such as international mobile equipment identification (IMEI) code, capable of uniquely identifying itself. For example, the processor 210, using the stored instructions, may determine an identity, e.g., using cell identification information.

Medical monitoring device 205 further comprises a user interface 215, which may include at least one input and/or output device coupled with processor 210 such as but not limited to a display, touch screen, keyboard, keypad, mouse and/or the like. In the embodiment, display 220 coupled with processor 210 and ECG signal simulator 255 is capable of displaying at least one of a simulated electrocardiogram signal, CPR artifact signal and an output of a signal modifier. In an embodiment, a keypad or keyboard enables a user to configure an ECG simulator such as ECG simulator 255 to produce at least one waveform such as but not limited to ventricular fibrillation (fine and course), ventricular tachycardia, atrial fibrillation, atrial ventricular block (third degree), absolute arrhythmia, pulseless electrical activity, asystole, and normal sinus rhythm. Further, the keypad or keyboard may enable a user to compose text-based messages and communicate with other users such as emergency medical personnel. In an embodiment, medical monitoring device 205 further comprises a speaker 217 and/or a microphone 280. Speaker 217, for example, may enable the medical monitoring device to provide voice instructions to a user. Microphone 280, for example, may enable a user to speak with emergency medical personnel via network interface 214 at an emergency response facility.

System 200 further comprises a chest compression sensor such as chest compression sensor 273 configured to detect at least one parameter corresponding to chest compressions of a subject. The at least one parameter may be at least one of acceleration, velocity, displacement amplitude and rate of chest compressions. In an embodiment, chest compression sensor 273 communicates the at least one parameter with processor 210 through chest compression sensor interface 270. Further, processor 210 may display the at least one parameter to a user via user interface 215 and/or display 220. In an embodiment, processer 210 may instruct ECG signal simulator to combine the at least one parameter from chest compression sensor 273 such as but not limited to acceleration or velocity with the output of the ECG signal simulator 255. The resulting ECG simulated signal with CPR artifact may be displayed by display 220, through user interface 215 or sent remotely through network interface 214.

In an embodiment, medical monitoring device 205 further comprises at least one power supply such as battery 205 for providing power to medical monitoring device and/or for charging defibrillation unit 235. Medical monitoring device 205 may further comprise a location determining unit 240. Location determining unit 240 may comprise a global positioning system (GPS) receiver for receiving a geographic location of medical monitoring device 205. Location determining unit 240 may use cell identification information to determine a geographic location for medical monitoring device 205.

In an embodiment, system 200 further comprises electrodes 277 electrically coupled with medical monitoring device 205. In an embodiment, electrodes 277 are electrodes 171 of FIG. 2. In the embodiment, electrodes 277 are electrically and physically connected with electrode interface 275. Processor 210 may monitor a subject's ECG signal through electrodes 277. Defibrillation unit 235 may analyze a subject's ECG signal and determine whether or not to provide a defibrillation shock to the subject using electrodes 277. In an embodiment, CPR artifact reduction unit 250 may monitor signals from chest compression sensor 273 through chest compression sensor interface 270 and filter at least some of the CPR artifact from an ECG waveform received through electrodes interface 275.

In an embodiment, medical monitoring device 205 further comprises a carbon dioxide monitoring unit 260 coupled with processor 210 configured to monitor a subject's end tidal carbon dioxide ($EtCO_2$). Medical monitoring device 205 may monitor a subject's other physiological parameters. For example, in an embodiment, medical monitoring device 205 comprises a pulse oximeter configured to measure a subject's oxygen saturation $SpO_2$.

FIG. 8 is a flow diagram depicting a method 800 according to an example embodiment of the invention. In an embodiment, at 805 a simulated ECG signal is generated by an ECG signal simulator such as ECG signal simulator 115a of FIG. 1, ECG signal simulator 300 of FIG. 5 and ECG signal generator 255 of FIG. 7. The simulated ECG signal may be but is not limited to one of ventricular fibrillation (fine and course), ventricular tachycardia, atrial fibrillation, atrial ventricular block (third degree), absolute arrhythmia, pulseless electrical activity, asystole, and normal sinus rhythm.

At 810, an output of a chest compression sensor is received by the ECG signal simulator. The chest compression sensor is configured to detect at least one parameter corresponding to chest compressions of a subject. The chest compression sensor may be but is not limited to chest compression sensor 120 of FIGS. 1 and 4, chest compression sensor 180 of FIG. 2, chest compression sensor 315 of FIG. 5 or chest compression sensor 273 of FIG. 6. The at least one parameter may be but is not limited to acceleration, velocity, displacement, amplitude and rate of chest compressions.

At 815, the simulated ECG signal is modified or combined with an output of the chest compression sensor to produce a simulated electrocardiogram signal with a CPR artifact. The simulated ECG signal may be modified by signal modifier 312 of FIG. 5 to include a chest compression signal component correlated with the actual rate and depth of compressions being performed. As previously disclosed, the signal modification can be performed in accordance with the teaching of the '413 patent or any similar or appropriate technique. The influence of the CPR compressions can be modeled as the output of a linear system perturbed by the actual chest compression sensor signal. For example, output of a chest compression sensor can be summed with the simulated ECG signal to produce a simulated ECG signal with CPR artifact, which tracks the influence of the actual CPR compressions being performed.

At 820, at least one of the simulated ECG signal, CPR artifact, output of the chest compression sensor and the simulated ECG signal may be displayed. One or more of the signals may be displayed by any display capable of displaying an ECG signal, for example, a medical monitoring device or device 125a of FIG. 1.

At 825, a CPR artifact may be filtered from a simulated ECG signal and the filtered ECG signal may be displayed. The CPR artifact may be filtered in any manner such as but not limited to utilizing the See-Thru CPR filtering techniques and methods developed by Zoll Medical Corporation of Chelmsford, Mass.

Without in any way limiting the scope, interpretation, or application of the claims appearing below, a technical effect of one or more of the example embodiments disclosed herein is to provide system for CPR training. The CPR training system allows a user to perform chest compressions on a subject and view one or more simulated ECG waveforms complicated by a true ECG artifact signal, which tracks the influence of the actual CPR compressions being performed. Another technical effect of one or more of the example embodiments disclosed herein is to provide a method for training a user to perform CPR on a subject and observe a number of possible ECG waveforms complicated by CPR artifact. Another technical effect of one or more of the example embodiments disclosed herein is to provide a method for training a user to observe a number of possible ECG waveforms complicated by a CPR artifact and removal or substantial reduction thereof.

Embodiments of the present invention may be implemented in software, firmware, hardware, application logic or a combination of software, hardware and application logic. The software, firmware, application logic and/or hardware may reside on at least one of system such as system 115a of FIG. 1, system 125b of FIG. 4, system 300 of FIG. 5 and system 200 of FIG. 7. If desired, part of the software, application logic and/or hardware may reside on system such as system 205 of FIG. 7 and part of the software, application logic and/or hardware may reside on system such as system 255 of FIG. 7. In an embodiment, the application logic, software or an instruction set is maintained on any one of various conventional computer-readable media. In the context of this document, a "computer-readable medium" may be any media or means that can contain, store, communicate, propagate or transport the instructions for use by or in connection with an instruction execution system, apparatus, or device, such as a computer, with one example of a computer described and depicted in FIG. 7. A computer-readable medium may comprise a computer-readable storage medium that may be any media or means that can contain or store the instructions for use by or in connection with an instruction execution system, apparatus, or device, such as a computer.

If desired, the different functions discussed herein may be performed in a different order and/or concurrently with each other. Furthermore, if desired, one or more of the above-described functions may be optional or may be combined.

Although various aspects of the invention are set out in the independent claims, other aspects of the invention comprise other combinations of features from the described embodiments and/or the dependent claims with the features of the independent claims, and not solely the combinations explicitly set out in the claims. It is also noted herein that while the above describes example embodiments of the invention, these descriptions should not be viewed in a limiting sense. Rather, there are several variations and modifications which may be made without departing from the scope of the present invention as defined in the appended claims.

What is claimed is:

1. A cardio-pulmonary resuscitation (CPR) training system, comprising: a chest compression sensor configured to detect at least one parameter corresponding to chest compressions of a mannequin and generate a chest compression signal; and an electrocardiogram signal simulator comprising a transfer function with a single input to the transfer function, the electrocardiogram signal simulator configured to: receive the chest compression signal from the chest compression sensor as the single input to the transfer function; generate a first electrocardiogram signal representative of cardiac-induced electrical activity; and generate a modification signal that acts upon the first electrocardiogram signal to create a second, modified electrocardiogram signal that simulates an electrocardiogram signal of a patient undergoing chest compressions during cardiac arrest, the modification signal simulating a compression-induced artifact that would be present in a measured electrocardiogram signal in a non-simulated environment as a result of mechanical disturbances from the chest compressions, wherein the modification signal is based on the chest compression signal and is generated at least in part by applying the transfer function to the chest compression signal.

2. The CPR training system of claim 1, comprising a display coupled with the electrocardiogram signal simulator, the display configured to present at least one of the first electrocardiogram signal, the modification signal, the second, modified electrocardiogram signal, the compression-induced artifact, and an output of the chest compression sensor.

3. The CPR training system of claim 2, wherein the second, modified electrocardiogram signal includes the compression-induced artifact, the compression-induced artifact being synchronized with the chest compressions of the mannequin and correlated to a depth and rate of the chest compressions of the mannequin.

4. The CPR training system of claim 1, wherein the electrocardiogram signal simulator is disposed within a medical monitoring device.

5. The CPR training system of claim 4, wherein the medical monitoring device comprises a defibrillator.

6. The CPR training system of claim 1, wherein the first electrocardiogram signal simulates at least one of ventricular fibrillation, ventricular tachycardia, atrial fibrillation, atrial ventricular block third degree, absolute arrhythmia, pulseless electrical activity, asystole and normal sinus rhythm.

7. The CPR training system of claim 1, wherein the at least one parameter is at least one of acceleration, velocity, displacement, amplitude and rate of chest compressions.

8. The CPR training system of claim 1, comprising an artifact reduction unit configured to remove the compression-induced artifact from the second, modified electrocardiogram signal.

9. The CPR training system of claim 1, wherein the CPR training system comprises a medical monitoring device.

10. The CPR training system of claim 9, wherein the medical monitoring device is configured to generate the first electrocardiogram signal when operating in a training mode and not generate the first electrocardiogram signal when operating in a normal mode.

11. The CPR training system of claim 1, comprising a display coupled with the electrocardiogram signal simulator, the display configured to present the first electrocardiogram signal and the second, modified electrocardiogram signal.

12. The CPR training system of claim 1, wherein the electrocardiogram signal simulator is configured to remove the compression-induced artifact from the second, modified electrocardiogram signal to generate a filtered electrocardiogram signal, and wherein the CPR training system comprises a display configured to present the first electrocardiogram signal, the modification signal, the second, modified electrocardiogram signal, the compression-induced artifact, and the filtered electrocardiogram signal.

13. The CPR training system of claim 1, wherein the modification signal simulates a compression-induced artifact caused by changes in half-cell potential of electrodes of a medical monitoring device used to measure the measured electrocardiogram signal in the non-simulated environment.

14. The CPR training system of claim 1, wherein the compression-induced artifact is consistent with characteristics of the chest compressions of the mannequin.

15. The CPR training system of claim 1, comprising a display coupled with the electrocardiogram signal simulator, the display configured to present the compression-induced artifact.

16. The CPR training system of claim 1, wherein the electrocardiogram signal simulator is configured to combine the first electrocardiogram signal and the modification signal to produce the second, modified electrocardiogram signal that includes the compression-induced artifact.

17. A method for training a rescuer to perform cardio-pulmonary resuscitation (CPR), comprising: generating a first electrocardiogram signal representative of cardiac-induced electrical activity; receiving a chest compression signal from a chest compression sensor as a single input to a transfer function, the chest compression sensor configured to detect at least one parameter corresponding to chest compressions of a mannequin; generating a modification signal that acts upon the first electrocardiogram signal to create a second, modified electrocardiogram signal that simulates an electrocardiogram signal of a patient undergoing chest compressions during cardiac arrest, the modification signal simulating a compression-induced artifact that would be present in a measured electrocardiogram signal in a non-simulated environment as a result of mechanical disturbances from the chest compressions, wherein the modification signal is based on the chest compression signal and is generated at least in part by applying the transfer function to the chest compression signal; and presenting at least one of the first electrocardiogram signal, the modification signal, the second, modified electrocardiogram signal, the compression-induced artifact, and an output of the chest compression sensor.

18. The method of claim 17, wherein the presenting is performed by a medical monitoring device.

19. The method of claim 17, wherein the first electrocardiogram signal simulates at least one of ventricular fibrillation, ventricular tachycardia, atrial fibrillation, atrial ventricular block third degree, absolute arrhythmia, pulseless electrical activity, asystole, and normal sinus rhythm.

20. The method of claim 17, wherein the at least one parameter comprises an indication of at least one of acceleration, velocity, displacement, amplitude and rate of chest compressions.

21. The method of claim 17, comprising filtering the compression-induced artifact from the second, modified electrocardiogram signal.

22. The method of claim 21, comprising presenting a filtered electrocardiogram signal.

23. The method of claim 17, wherein at least one of the generating the first electrocardiogram signal and generating the modification signal is performed by an electrocardiogram signal simulator.

24. The method of claim 23, wherein the electrocardiogram signal simulator is disposed within a medical monitoring device configured to generate the first electrocardiogram signal when operating in a training mode and not generate the first electrocardiogram signal when operating in a normal mode.

25. The method of claim 24, wherein the medical monitoring device comprises a defibrillator.

26. A cardio-pulmonary resuscitation (CPR) training system, comprising: at least one processor; and at least one memory including computer program code; the at least one memory and the computer program code configured with the at least one processor to cause the system to: generate a first electrocardiogram signal representative of cardiac induced electrical activity; receive a chest compression signal from a chest compression sensor as a single input to a transfer function, the chest compression sensor configured to detect at least one parameter corresponding to chest compressions of a mannequin; generate a modification signal that acts upon the first electrocardiogram signal to create a second, modified electrocardiogram signal that simulates an electrocardiogram signal of a patient undergoing chest compressions during cardiac arrest, the modification signal simulating a compression-induced artifact that would be present in a measured electrocardiogram signal in a non-simulated environment as a result of mechanical disturbances from the chest compressions, wherein the modification signal is based on the chest compression signal and is generated at least in part by applying the transfer function to the chest compression signal; and present at least one of the first electrocardiogram signal, the modification signal, the second, modified electrocardiogram signal, the compression-induced artifact, and an output of the chest compression sensor.

27. The CPR training system of claim 26, wherein the at least one parameter is at least one of acceleration, velocity, displacement, amplitude and rate of chest compressions.

28. The CPR training system of claim 26, wherein the at least one memory and the computer program code is configured with the at least one processor to cause the system to filter the compression-induced artifact from the second, modified electrocardiogram signal.

29. The CPR training system of claim 28, wherein the at least one memory and the computer program code is configured with the at least one processor to cause the system present a filtered electrocardiogram signal.

30. The CPR training system of claim 26, wherein the CPR training system is disposed within a medical monitoring device configured to generate the first electrocardiogram signal when operating in a training mode and not generate the first electrocardiogram signal when operating in a normal mode.

31. The CPR training system of claim 30, wherein the medical monitoring device comprises a defibrillator.

* * * * *